United States Patent
Houpis et al.

(10) Patent No.: US 10,544,184 B2
(45) Date of Patent: *Jan. 28, 2020

(54) URACYL SPIROOXETANE NUCLEOSIDES

(71) Applicant: Janssen Sciences Ireland Unlimited Company, County Cork (IE)

(72) Inventors: Ioannis Nicolaos Houpis, Antwerp (BE); Tim Hugo Maria Jonckers, Heist-op-den-Berg (BE); Pierre Jean-Marie Bernard Raboisson, Rosieres (BE); Abdellah Tahri, Anderlecht (BE)

(73) Assignee: Janssen Sciences Ireland Unlimited Company, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,351

(22) Filed: Apr. 12, 2019

(65) Prior Publication Data

US 2019/0241604 A1 Aug. 8, 2019

Related U.S. Application Data

(63) Continuation of application No. 16/212,554, filed on Dec. 6, 2018, now Pat. No. 10,301,347, which is a continuation of application No. 16/044,262, filed on Jul. 24, 2018, now abandoned, which is a continuation of application No. 15/809,730, filed on Nov. 10, 2017, now Pat. No. 10,040,814, which is a continuation of application No. 15/423,985, filed on Feb. 3, 2017, now Pat. No. 9,845,336, which is a continuation of application No. 15/238,553, filed on Aug. 16, 2016, now abandoned, which is a continuation of application No. 14/403,587, filed as application No. PCT/EP2013/060704 on May 24, 2013, now Pat. No. 9,422,323.

(30) Foreign Application Priority Data

May 25, 2012 (EP) .................... 12169425

(51) Int. Cl.
| | |
|---|---|
| C07H 19/06 | (2006.01) |
| C07H 1/00 | (2006.01) |
| C07H 19/10 | (2006.01) |
| C07H 19/11 | (2006.01) |
| A61K 31/7072 | (2006.01) |
| C07H 19/24 | (2006.01) |

(52) U.S. Cl.
CPC ......... *C07H 19/10* (2013.01); *A61K 31/7072* (2013.01); *C07H 1/00* (2013.01); *C07H 19/06* (2013.01); *C07H 19/11* (2013.01); *C07H 19/24* (2013.01)

(58) Field of Classification Search
None
See application file for complete search history.

(56) References Cited

U.S. PATENT DOCUMENTS

| | | | |
|---|---|---|---|
| 3,480,613 | A | 11/1969 | Walton et al. |
| 3,817,978 | A | 6/1974 | Jenkins et al. |
| 3,852,267 | A | 12/1974 | Meyer, Jr. et al. |
| 4,713,383 | A | 12/1987 | Francis et al. |
| 5,049,551 | A | 9/1991 | Koda et al. |
| 5,679,342 | A | 10/1997 | Houghton et al. |
| 5,712,088 | A | 1/1998 | Houghton et al. |
| 5,714,596 | A | 2/1998 | Houghton et al. |
| 5,863,719 | A | 1/1999 | Houghton et al. |
| 6,027,729 | A | 2/2000 | Houghton et al. |
| 6,074,816 | A | 6/2000 | Houghton et al. |
| 6,096,541 | A | 8/2000 | Houghton et al. |
| 6,171,782 | B1 | 1/2001 | Houghton et al. |
| 6,174,868 | B1 | 1/2001 | Anderson et al. |

(Continued)

FOREIGN PATENT DOCUMENTS

| | | |
|---|---|---|
| AU | 51819/98 | 11/1998 |
| CA | 2026131 | 3/1991 |

(Continued)

OTHER PUBLICATIONS

U.S. Appl. No. 11/005,443, filed Dec. 6, 2004, LaColla et al.

(Continued)

*Primary Examiner* — Traviss C McIntosh, III

(57) ABSTRACT

The present invention relates to compound of the formula I:

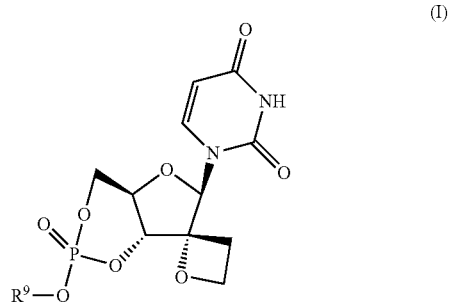

including any possible stereoisomers thereof, wherein $R^9$ has the meaning as defined herein, or a pharmaceutically acceptable salt or solvate thereof. The present invention also related to processes for preparing said compounds, pharmaceutical compositions containing them and their use, alone or in combination with other HCV inhibitors, in HCV therapy.

4 Claims, 1 Drawing Sheet

Specification includes a Sequence Listing.

(56) References Cited

U.S. PATENT DOCUMENTS

| | | |
|---|---|---|
| 6,284,458 B1 | 9/2001 | Anderson et al. |
| 6,348,587 B1 | 2/2002 | Schinazi et al. |
| 6,391,542 B1 | 5/2002 | Anderson et al. |
| 6,423,489 B1 | 7/2002 | Anderson et al. |
| 6,433,159 B1 | 8/2002 | Anderson |
| 6,455,513 B1 | 9/2002 | McGuigan et al. |
| 6,495,677 B1 | 12/2002 | Ramasamy et al. |
| 6,566,365 B1 | 5/2003 | Storer |
| 6,573,247 B1 | 6/2003 | McGuigan et al. |
| 6,608,191 B1 | 8/2003 | Anderson et al. |
| 6,638,919 B2 | 10/2003 | McGuigan et al. |
| 6,660,721 B2 | 12/2003 | Devos et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,525 B1 | 9/2004 | Schott et al. |
| 6,800,751 B2 | 10/2004 | Sanghvi et al. |
| 6,812,219 B2 | 11/2004 | LaColla et al. |
| 6,833,361 B2 | 12/2004 | Hong et al. |
| 6,846,810 B2 | 1/2005 | Martin et al. |
| 6,897,302 B2 | 5/2005 | Kowalczyk et al. |
| 6,911,424 B2 | 6/2005 | Schinazi et al. |
| 6,914,054 B2 | 7/2005 | Sommadossi et al. |
| 6,927,291 B2 | 8/2005 | Jin et al. |
| 6,995,146 B2 | 2/2006 | Anderson et al. |
| 7,018,989 B2 | 3/2006 | McGuigan et al. |
| 7,019,135 B2 | 3/2006 | McGuigan et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,115,590 B1 | 10/2006 | Daluge et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,300,924 B2 | 11/2007 | Boojamra et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,339,054 B2 | 3/2008 | Xu et al. |
| 7,365,057 B2 | 4/2008 | LaColla et al. |
| 7,378,402 B2 | 5/2008 | Martin et al. |
| 7,384,924 B2 | 6/2008 | LaColla et al. |
| 7,405,204 B2 | 7/2008 | Roberts et al. |
| 7,429,572 B2 | 9/2008 | Clark |
| 7,452,901 B2 | 11/2008 | Boojamra et al. |
| 7,456,155 B2 | 11/2008 | Sommadossi et al. |
| 7,524,825 B2 | 4/2009 | Keicher et al. |
| 7,534,767 B2 | 5/2009 | Butora et al. |
| 7,547,704 B2 | 6/2009 | LaColla et al. |
| 7,582,618 B2 | 9/2009 | Sommadossi et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,632,940 B2 | 12/2009 | Harrington et al. |
| 7,635,689 B2 | 12/2009 | LaColla et al. |
| 7,645,745 B2 | 1/2010 | Sarma |
| 7,645,747 B2 | 1/2010 | Boojamra et al. |
| 7,662,798 B2 | 2/2010 | LaColla et al. |
| 7,666,856 B2 | 2/2010 | Johansson et al. |
| 7,741,334 B2 | 6/2010 | Pottage |
| 7,754,699 B2 | 7/2010 | Chun et al. |
| 7,772,208 B2 | 8/2010 | Schinazi et al. |
| 7,781,576 B2 | 8/2010 | Mayes et al. |
| 7,790,366 B1 | 9/2010 | Houghton et al. |
| 7,820,631 B2 | 10/2010 | McGuigan et al. |
| 7,824,851 B2 | 11/2010 | Sommadossi et al. |
| 7,842,672 B2 | 11/2010 | Boojamra et al. |
| 7,871,991 B2 | 1/2011 | Boojamra et al. |
| 7,879,815 B2 | 2/2011 | MacCoss et al. |
| 7,902,202 B2 | 3/2011 | Sommadossi et al. |
| 7,915,232 B2 | 3/2011 | Martin et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,022,083 B2 | 9/2011 | Boojamra et al. |
| 8,071,567 B2 | 12/2011 | Devos et al. |
| 8,119,779 B2 | 2/2012 | McGuigan et al. |
| 8,148,349 B2 | 4/2012 | Meppen et al. |
| 8,168,583 B2 | 5/2012 | Schinazi et al. |
| 8,173,621 B2 | 5/2012 | Du et al. |
| 8,183,216 B2 | 5/2012 | Di Francesco et al. |
| 8,236,779 B2 | 8/2012 | Ma et al. |
| 8,299,038 B2 | 10/2012 | Sommadossi et al. |
| 8,318,682 B2 | 11/2012 | Butler et al. |
| 8,318,701 B2 | 11/2012 | Boojamra et al. |
| 8,324,179 B2 | 12/2012 | Chen et al. |
| 8,329,926 B2 | 12/2012 | Boojamra et al. |
| 8,334,270 B2 | 12/2012 | Sofia et al. |
| 8,399,428 B2 | 3/2013 | Wagner |
| 8,399,429 B2 | 3/2013 | Jonckers et al. |
| 8,404,651 B2 | 3/2013 | Iyer et al. |
| 8,415,308 B2 | 4/2013 | Cho et al. |
| 8,415,321 B2 | 4/2013 | Schinazi et al. |
| 8,415,322 B2 | 4/2013 | Clark |
| 8,507,460 B2 | 4/2013 | Surleraux et al. |
| 8,455,451 B2 | 6/2013 | Cho et al. |
| 8,481,510 B2 | 7/2013 | Jonckers et al. |
| 8,481,713 B2 | 7/2013 | Wang et al. |
| 8,551,973 B2 | 10/2013 | Baa et al. |
| 8,552,021 B2 | 10/2013 | Jonckers et al. |
| 8,563,530 B2 | 10/2013 | Chang et al. |
| 8,569,478 B2 | 10/2013 | Du et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,716,263 B2 | 5/2014 | Chun et al. |
| 8,728,725 B2 | 5/2014 | Paul et al. |
| 8,735,372 B2 | 5/2014 | Du et al. |
| 8,759,318 B2 | 6/2014 | Chamberlain et al. |
| 8,759,510 B2 | 6/2014 | Du et al. |
| 8,765,710 B2 | 7/2014 | Sofia et al. |
| 8,765,935 B2 | 7/2014 | Wagner |
| 8,772,474 B2 | 7/2014 | Beigelman et al. |
| 8,802,840 B2 | 8/2014 | Francom et al. |
| 8,816,074 B2 | 8/2014 | Chu et al. |
| 8,841,275 B2 | 9/2014 | Du et al. |
| 8,859,756 B2 | 10/2014 | Ross et al. |
| 8,871,737 B2 | 10/2014 | Smith et al. |
| 8,877,731 B2 | 11/2014 | Beigelman et al. |
| 8,877,733 B2 | 11/2014 | Cho et al. |
| 8,933,052 B2 | 1/2015 | Jonckers et al. |
| 8,980,865 B2 | 3/2015 | Wang et al. |
| 9,422,323 B2 | 8/2016 | Houpis et al. |
| 9,845,336 B2 | 12/2017 | Houpis et al. |
| 10,040,814 B2 * | 8/2018 | Houpis ............... C07H 19/11 |
| 2003/0008841 A1 | 1/2003 | Devos et al. |
| 2003/0087873 A1 | 5/2003 | Stuyver et al. |
| 2003/0129712 A1 | 7/2003 | Poechlauer et al. |
| 2003/0236216 A1 | 12/2003 | Devos et al. |
| 2004/0002596 A1 | 1/2004 | Hong et al. |
| 2004/0006002 A1 | 1/2004 | Sommadossi et al. |
| 2004/0014108 A1 | 1/2004 | Eldrup et al. |
| 2004/0110718 A1 | 6/2004 | Devos et al. |

(56) References Cited

U.S. PATENT DOCUMENTS

| | | |
|---|---|---|
| 2004/0121980 A1 | 6/2004 | Martin et al. |
| 2004/0181052 A1 | 9/2004 | Sourena et al. |
| 2004/0209904 A1 | 10/2004 | Dunn et al. |
| 2004/0229839 A1 | 11/2004 | Babu et al. |
| 2004/0229840 A1 | 11/2004 | Bhat et al. |
| 2004/0259934 A1 | 12/2004 | Olsen et al. |
| 2004/0266723 A1 | 12/2004 | Otto et al. |
| 2005/0009737 A1 | 1/2005 | Clark |
| 2005/0009775 A1 | 1/2005 | Howes et al. |
| 2005/0038240 A1 | 2/2005 | Connolly et al. |
| 2005/0124532 A1 | 6/2005 | Sommadossi et al. |
| 2006/0040890 A1 | 2/2006 | Martin et al. |
| 2006/0040944 A1 | 2/2006 | Gosselin et al. |
| 2006/0205685 A1 | 9/2006 | Phiasivongsa et al. |
| 2006/0234962 A1 | 10/2006 | Olsen et al. |
| 2006/0264389 A1 | 11/2006 | Bhat et al. |
| 2007/0004669 A1 | 1/2007 | Carroll et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042988 A1 | 2/2007 | Klumpp et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0265222 A1 | 11/2007 | MacCoss et al. |
| 2008/0070861 A1 | 3/2008 | Clark |
| 2008/0139802 A1 | 6/2008 | Axt et al. |
| 2008/0207554 A1 | 8/2008 | Beigelman et al. |
| 2008/0253995 A1 | 10/2008 | Clark |
| 2008/0255038 A1 | 10/2008 | Hopkins et al. |
| 2008/0261913 A1 | 10/2008 | Sommadossi et al. |
| 2008/0280842 A1 | 11/2008 | MacCoss et al. |
| 2008/0286230 A1 | 11/2008 | Sommadossi et al. |
| 2009/0004135 A1 | 1/2009 | Clark |
| 2009/0036666 A1 | 2/2009 | Clark |
| 2009/0048189 A1 | 2/2009 | Keicher et al. |
| 2009/0076062 A1 | 3/2009 | Maibaum et al. |
| 2009/0118223 A1 | 5/2009 | Erion et al. |
| 2009/0162292 A1 | 6/2009 | Thompson et al. |
| 2009/0169504 A1 | 7/2009 | Sommadossi et al. |
| 2009/0176732 A1 | 7/2009 | Beigelman et al. |
| 2009/0181921 A1 | 7/2009 | Blatt et al. |
| 2009/0238790 A2 | 9/2009 | Sommadossie et al. |
| 2009/0306007 A1 | 12/2009 | Wagner |
| 2009/0318380 A1 | 12/2009 | Sofia et al. |
| 2010/0003217 A1 | 1/2010 | Cretton-Scott et al. |
| 2010/0056468 A1 | 3/2010 | Kotra et al. |
| 2010/0077085 A1 | 3/2010 | Cohen |
| 2010/0081628 A1 | 4/2010 | Du et al. |
| 2010/0151001 A1 | 6/2010 | Schott et al. |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0279973 A1 | 11/2010 | Chun et al. |
| 2010/0279974 A1 | 11/2010 | Pierra et al. |
| 2010/0286083 A1 | 11/2010 | Bao et al. |
| 2010/0297079 A1 | 11/2010 | Almond et al. |
| 2010/0298257 A1 | 11/2010 | Ross et al. |
| 2010/0316594 A1 | 12/2010 | Sommadossi et al. |
| 2010/0331397 A1 | 12/2010 | Beigelman et al. |
| 2011/0015146 A1 | 1/2011 | Sofia et al. |
| 2011/0021454 A1 | 1/2011 | Du et al. |
| 2011/0091943 A1 | 4/2011 | Gallou et al. |
| 2011/0124592 A1 | 5/2011 | McGuigan et al. |
| 2011/0150997 A1 | 6/2011 | Shah et al. |
| 2011/0171192 A1 | 7/2011 | Tomiyama et al. |
| 2011/0217261 A1 | 9/2011 | Or et al. |
| 2011/0243886 A1 | 10/2011 | Surleraux et al. |
| 2011/0244027 A1 | 10/2011 | Chu et al. |
| 2011/0245484 A1 | 10/2011 | Ross et al. |
| 2011/0251152 A1 | 10/2011 | Ross et al. |
| 2011/0257121 A1 | 10/2011 | Chang et al. |
| 2011/0269707 A1 | 11/2011 | Stuyver et al. |
| 2011/0286962 A1 | 11/2011 | Sommadossi et al. |
| 2011/0287927 A1 | 11/2011 | Grasset et al. |
| 2011/0288308 A1 | 11/2011 | Grasset et al. |
| 2011/0306541 A1 | 12/2011 | Delaney, IV et al. |
| 2011/0306573 A1 | 12/2011 | Avolio et al. |
| 2012/0010164 A1 | 1/2012 | Surnma et al. |
| 2012/0034184 A1 | 2/2012 | Devos et al. |
| 2012/0035115 A1 | 2/2012 | Manoharan et al. |
| 2012/0040924 A1 | 2/2012 | Cho et al. |
| 2012/0041184 A1 | 2/2012 | Beigelman et al. |
| 2012/0052046 A1 | 3/2012 | Chamberlain et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0107274 A1 | 5/2012 | Clarke et al. |
| 2012/0142626 A1 | 6/2012 | Du et al. |
| 2012/0157511 A1 | 6/2012 | Manoharan et al. |
| 2012/0165286 A1 | 6/2012 | Beigelman et al. |
| 2012/0165515 A1 | 6/2012 | Bhat et al. |
| 2012/0219568 A1 | 8/2012 | Liu et al. |
| 2012/0225839 A1 | 9/2012 | Jonckers et al. |
| 2012/0232029 A1 | 9/2012 | Sofia et al. |
| 2012/0237480 A1 | 9/2012 | Or et al. |
| 2012/0245335 A1 | 9/2012 | Clark |
| 2012/0251487 A1 | 10/2012 | Surleraux |
| 2012/0258928 A1 | 10/2012 | Du et al. |
| 2012/0263678 A1 | 10/2012 | Cho et al. |
| 2012/0316327 A1 | 12/2012 | Chun et al. |
| 2013/0005677 A1 | 1/2013 | Chu et al. |
| 2013/0017171 A1 | 1/2013 | Sommadossi et al. |
| 2013/0029929 A1 | 1/2013 | Sofia et al. |
| 2013/0064793 A1 | 3/2013 | Surleraux et al. |
| 2013/0078217 A1 | 3/2013 | Wang et al. |
| 2013/0137143 A1 | 5/2013 | Gallou et al. |
| 2013/0149283 A1 | 6/2013 | Sommadossi et al. |
| 2013/0164261 A1 | 6/2013 | Wang et al. |
| 2013/0165400 A1 | 6/2013 | Beigelman et al. |
| 2013/0203978 A1 | 8/2013 | Wagner |
| 2013/0225520 A1 | 8/2013 | Jonckers et al. |
| 2013/0244968 A1 | 9/2013 | Jonckers et al. |
| 2013/0252920 A1 | 9/2013 | Blatt et al. |
| 2013/0253181 A1 | 9/2013 | Serebryany et al. |
| 2013/0273005 A1 | 10/2013 | Delaney et al. |
| 2013/0281686 A1 | 10/2013 | Cho et al. |
| 2013/0281687 A1 | 10/2013 | Serebryany et al. |
| 2013/0315862 A1 | 11/2013 | Sommadossi et al. |
| 2013/0315866 A1 | 11/2013 | Parsy et al. |
| 2013/0315867 A1 | 11/2013 | Parsy et al. |
| 2013/0315868 A1 | 11/2013 | Mayes et al. |
| 2013/0323836 A1 | 12/2013 | Manoharan et al. |
| 2013/0330297 A1 | 12/2013 | Storer et al. |
| 2014/0045783 A1 | 2/2014 | Du et al. |
| 2014/0057863 A1 | 2/2014 | Stuyver et al. |
| 2014/0086873 A1 | 3/2014 | Mayes et al. |
| 2014/0088117 A1 | 3/2014 | Burch et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0140955 A1 | 5/2014 | McGuigan et al. |
| 2014/0154211 A1 | 6/2014 | Girijavallabhan et al. |
| 2014/0161770 A1 | 6/2014 | Girijavallabhan et al. |
| 2014/0178338 A1 | 6/2014 | Mayes et al. |
| 2014/0179627 A1 | 6/2014 | Beigelman et al. |
| 2014/0205566 A1 | 7/2014 | Liao et al. |
| 2014/0206640 A1 | 7/2014 | Girijavallabhan et al. |
| 2014/0212382 A1 | 7/2014 | Schinazi et al. |
| 2014/0219958 A1 | 8/2014 | Luly et al. |
| 2014/0221304 A1 | 8/2014 | Verma et al. |
| 2014/0235567 A1 | 8/2014 | Verma et al. |
| 2014/0271547 A1 | 9/2014 | Dukhan et al. |
| 2014/0288020 A1 | 9/2014 | Du et al. |
| 2014/0294769 A1 | 10/2014 | Mayes et al. |
| 2014/0303113 A1 | 10/2014 | Krop et al. |
| 2014/0309164 A1 | 10/2014 | Deshpande et al. |

(56) References Cited

U.S. PATENT DOCUMENTS

| | | |
|---|---|---|
| 2014/0309189 A1 | 10/2014 | Deshpande et al. |
| 2014/0315850 A1 | 10/2014 | Huang et al. |
| 2014/0315852 A1 | 10/2014 | Du et al. |
| 2015/0018300 A1 | 1/2015 | Du et al. |
| 2017/0029455 A1 | 2/2017 | Houpis et al. |
| 2018/0327441 A1 | 11/2018 | Houpis et al. |
| 2019/0092804 A1 | 3/2019 | Houpis et al. |

FOREIGN PATENT DOCUMENTS

| | | |
|---|---|---|
| CA | 2087967 | 1/1992 |
| CA | 2600359 A1 | 9/2006 |
| CN | 1133642 C | 1/2004 |
| CN | 103102345 | 5/2013 |
| CN | 103848876 A | 6/2014 |
| CN | 103848877 A | 6/2014 |
| DE | 4232852 | 3/1994 |
| DE | 19855963 | 6/2000 |
| DE | 20121305 A2 | 9/2002 |
| EP | 1178049 | 2/2002 |
| EP | 1323830 | 7/2003 |
| EP | 1980568 A1 | 10/2008 |
| EP | 2264169 A1 | 12/2010 |
| EP | 2266579 A1 | 12/2010 |
| EP | 2388069 A1 | 11/2011 |
| EP | 2392580 | 12/2011 |
| FR | 2977586 | 1/2013 |
| IN | 167775 | 12/1990 |
| JP | 05069681 | 3/1993 |
| JP | 07242544 | 9/1995 |
| JP | 2008214305 | 9/2008 |
| WO | WO 93/16075 A1 | 8/1993 |
| WO | WO 1993/017651 A2 | 9/1993 |
| WO | WO 94/28715 A1 | 12/1994 |
| WO | WO 95/08540 A1 | 3/1995 |
| WO | WO 95/15332 A1 | 6/1995 |
| WO | WO 97/26883 A1 | 7/1997 |
| WO | WO 98/16184 A2 | 4/1998 |
| WO | WO 98/16186 A2 | 4/1998 |
| WO | WO 99/14226 A2 | 3/1999 |
| WO | WO 99/61583 A2 | 12/1999 |
| WO | WO 2000/034276 A1 | 6/2000 |
| WO | WO 2000/066604 A2 | 11/2000 |
| WO | WO 2001/068663 A1 | 9/2001 |
| WO | WO 2002/003997 A1 | 1/2002 |
| WO | WO 2002/057287 A2 | 7/2002 |
| WO | WO 2002/057425 A2 | 7/2002 |
| WO | WO 2002/100415 A2 | 12/2002 |
| WO | WO 2003/022859 A2 | 3/2003 |
| WO | WO 2003/026589 A2 | 4/2003 |
| WO | WO 2003/039523 A2 | 5/2003 |
| WO | WO 2003/048315 A2 | 6/2003 |
| WO | WO 2003/068244 A1 | 8/2003 |
| WO | WO 2003/073989 A2 | 9/2003 |
| WO | WO 2003/087119 A1 | 10/2003 |
| WO | WO 2003/099840 A1 | 12/2003 |
| WO | WO 2003/105770 A2 | 12/2003 |
| WO | WO 2004/002999 A2 | 1/2004 |
| WO | WO 2004/003138 A2 | 1/2004 |
| WO | WO 2004/007512 A2 | 1/2004 |
| WO | WO 2004/014312 A2 | 2/2004 |
| WO | WO 2004/037159 A2 | 5/2004 |
| WO | WO 2004/080466 A1 | 9/2004 |
| WO | WO 2004/091499 A2 | 10/2004 |
| WO | WO 2004/106356 A1 | 12/2004 |
| WO | WO 2005/007810 A2 | 1/2005 |
| WO | WO 2005/009418 A2 | 2/2005 |
| WO | WO 2005/020884 A2 | 3/2005 |
| WO | WO 2005/020885 A2 | 3/2005 |
| WO | WO 2005/021568 A2 | 3/2005 |
| WO | WO 2005/034878 A2 | 4/2005 |
| WO | WO 2006/000922 A2 | 1/2006 |
| WO | WO 2006/012078 | 2/2006 |
| WO | WO 2006/044968 A2 | 4/2006 |
| WO | WO 2006/063717 A2 | 6/2006 |
| WO | WO 2006/094347 A1 | 9/2006 |
| WO | WO 2006/105440 A2 | 10/2006 |
| WO | WO 2006/116512 A1 | 11/2006 |
| WO | WO 2007/027248 A2 | 3/2007 |
| WO | WO 2007/113538 A1 | 10/2007 |
| WO | WO 2008/012555 A2 | 1/2008 |
| WO | WO 2008/054808 A2 | 5/2008 |
| WO | WO 2008/089439 A2 | 7/2008 |
| WO | WO 2008/095040 A2 | 8/2008 |
| WO | WO 2008/117047 A1 | 10/2008 |
| WO | WO 2008/121634 A2 | 10/2008 |
| WO | WO 2009/001097 A2 | 12/2008 |
| WO | WO 2009/003042 A1 | 12/2008 |
| WO | WO 2009/010299 A1 | 1/2009 |
| WO | WO 2009/040269 A1 | 4/2009 |
| WO | WO 2009/058800 A2 | 5/2009 |
| WO | WO 2009/067409 | 5/2009 |
| WO | WO 2009/086201 A1 | 7/2009 |
| WO | WO 2009/105712 A1 | 8/2009 |
| WO | WO 2009/129120 A2 | 10/2009 |
| WO | WO 2009/152095 A2 | 12/2009 |
| WO | WO 2010/002877 A2 | 1/2010 |
| WO | WO 2010/026153 A1 | 3/2010 |
| WO | WO 2010/027005 A1 | 3/2010 |
| WO | WO 2010/075554 A1 | 7/2010 |
| WO | WO 2010/084115 A2 | 7/2010 |
| WO | WO 2010/088924 A1 | 8/2010 |
| WO | WO 2010/089128 A2 | 8/2010 |
| WO | WO 2010/091386 A2 | 8/2010 |
| WO | WO 2010/108140 | 9/2010 |
| WO | WO 2010/130726 A1 | 11/2010 |
| WO | WO 2011/005860 A2 | 1/2011 |
| WO | WO 2011/029537 A1 | 3/2011 |
| WO | WO 2011/057204 A2 | 5/2011 |
| WO | WO 2011/119869 A1 | 9/2011 |
| WO | WO 2011/133871 A2 | 10/2011 |
| WO | WO 2012/012465 A1 | 1/2012 |
| WO | WO 2012/012776 A1 | 1/2012 |
| WO | WO 2012/025857 A2 | 3/2012 |
| WO | WO 2012/041965 A1 | 4/2012 |
| WO | WO 2012/048013 A2 | 4/2012 |
| WO | WO 2012/062869 A1 | 5/2012 |
| WO | WO 2012/062870 A1 | 5/2012 |
| WO | WO 2012/074547 A2 | 6/2012 |
| WO | WO 2012/075140 A1 | 6/2012 |
| WO | WO 2012/092484 A2 | 7/2012 |
| WO | WO 2012/094248 A1 | 7/2012 |
| WO | WO 2012/099630 | 7/2012 |
| WO | WO 2012/142075 A1 | 10/2012 |
| WO | WO 2012/142085 A1 | 10/2012 |
| WO | WO 2012/142093 A2 | 10/2012 |
| WO | WO 2012/142523 A2 | 10/2012 |
| WO | WO 2012/158811 A2 | 11/2012 |
| WO | WO 2012/167133 A2 | 12/2012 |
| WO | WO 2013/009735 A1 | 1/2013 |
| WO | WO 2013/009737 A1 | 1/2013 |
| WO | WO 2013/013009 A2 | 1/2013 |
| WO | WO 2013/019874 A1 | 2/2013 |
| WO | WO 2013/071169 A1 | 5/2013 |
| WO | WO 2013/072466 A1 | 5/2013 |
| WO | WO 2013/087765 A1 | 6/2013 |
| WO | WO 2013/092447 A1 | 6/2013 |
| WO | WO 2013/092481 | 6/2013 |
| WO | WO 2013/106344 A1 | 7/2013 |
| WO | WO 2013/138210 A1 | 9/2013 |
| WO | WO 2013/142124 | 9/2013 |
| WO | WO 2013/142159 | 9/2013 |
| WO | WO 2013/142525 | 9/2013 |
| WO | WO 2013/174962 A1 | 11/2013 |
| WO | WO 2013/177219 A1 | 11/2013 |
| WO | WO 2014/008236 A1 | 1/2014 |
| WO | WO 2014/047117 A1 | 3/2014 |
| WO | WO 2014/048532 | 4/2014 |
| WO | WO 2014/059901 A1 | 4/2014 |
| WO | WO 2014/059902 A1 | 4/2014 |
| WO | WO 2014/062596 A1 | 4/2014 |
| WO | WO 2014/070771 A1 | 5/2014 |
| WO | WO 2014/099941 A1 | 6/2014 |
| WO | WO 2014/100498 A1 | 6/2014 |

(56) References Cited

FOREIGN PATENT DOCUMENTS

| | | |
|---|---|---|
| WO | WO 2014/100505 A1 | 6/2014 |
| WO | WO 2014/124430 A1 | 8/2014 |
| WO | WO 2014/164533 | 10/2014 |
| WO | WO 2014/169278 A2 | 10/2014 |
| WO | WO 2014/169280 A2 | 10/2014 |
| WO | WO 2014/186637 A1 | 11/2014 |
| WO | WO 2014/209979 A1 | 12/2014 |
| WO | WO 2014/209983 A1 | 12/2014 |
| WO | WO 2015/038596 A1 | 3/2015 |
| WO | WO 2015/054465 A1 | 4/2015 |
| WO | WO 2015/061683 A1 | 4/2015 |
| WO | WO 2015/081133 A2 | 6/2015 |

OTHER PUBLICATIONS

Lewis W, et al. "Mitochondrial toxicity of NRTI antiviral drugs: an integrated cellular perspective" Nature Reviews Drug Discovery (2003) 2:812-22.

Moyle G. "Clinical manifestations and management of antiretroviral nucleoside analog-related mitochondrial toxicity" Clin. Ther. (2000) 22(8):911-36.

Arnold et al.; "Sensitivity of Mitochondrial Transcription and Resistance of RNA Polymerase II Dependent Nuclear Transcription to Antiviral Ribonucleosides" PLOS | Pathogens (2012) 8(11) e1003030 (12 pages).

Lee et al.; "A Concise Synthesis of 4'-Fiuoro Nucleosides" Organic Letters (2007), 9(24), 5007-5009.

Owen et al.; "4'-Substituted nucleosides. Synthesis of some 4'-fluorouridine derivatives", J. Org. Chem. (1976), 41(18), 3010-17.

Congiatu et al., Novel Potential Anticancer Naphthyl Phosphoramidates of BVdU: Separation of Diastereoisomers and Assignment of the Absolute Configuration of the Phosphorus Center (2006) *Journal of Medicinal Chemistry* 49:452-455.

Eldrup et al., Structure-Activity Relationship of Purine Ribonucleosides for Inhibition of Hepatitis C Virus RNA-Dependent RNA Polymerase (2004) *Journal of Medicinal Chemistry* 47:2283-2295.

Gardelli et al., Phosphoramidate Prodrugs of 2'-C-Methylcytidine for Therapy of Hepatitis C Virus Infection (2009) *Journal of Medicinal Chemistry* 52:5394-5407.

Hollecker et al., Synthesis of -enantiomers of N4-hydroxy-3'-deoxypyrimidine nucleosides and their evaluation against bovine viral diarrhoea virus and hepatitis C virus in cell culture (2004) *Antiviral Chemistry & Chemotherapy* 14:43-55.

Ivanov et al., Synthesis and biological properties of pyrimidine 4'-fluoronucleosides and 4'-fluorouridine 5'-0-triphosphate (2010) *Russian Journal of Bioorganic Chemistry* 36:488-496.

King et al., Inhibition of the replication of a hepatitis C virus-like RNA template by interferon and 3'-deoxycytidine (2002) *Antiviral Chemistry & Chemotherapy* 13:363-370.

Leisvuori et al., Synthesis of 3',5'-Cyclic Phosphate and Thiophosphate Esters of 2'-C-Methyl Ribonucleosides (2012) *Helvetica Chimica Acta* 95:1512-1520.

McGuigan et al., Phosphoramidate ProTides of 2'-C-Methylguanosine as Highly Potent Inhibitors of Hepatitis C Virus. Study of Their in Vitro and in Vivo Properties (2010) *Journal of Medicinal Chemistry* 53:4949-4957.

McGuigan et al., Phosphorodiamidates as a Promising New Phosphate Prodrug Motif for Antiviral Drug Discovery: Application to Anti-HCV Agents (2011) *Journal of Medicinal Chemistry* 54:8632-8645.

McGuigan et al., The application of phosphoramidate ProTide technology to the potent anti-HCV compound 4'-azidocytidine (R1479) (2009) *Bioorganic & Medicinal Chemistry Letters* 19:4250-4254.

Mehellou et al., Phosphoramidates of 2'--D-arabinouridine (AraU) as phosphate prodrugs; design, synthesis, in vitro activity and metabolism (2010) *Bioorganic & Medicinal Chemistry* 18:2439-2446.

Mehellou et al., The design, synthesis and antiviral evaluation of a series of 5-trimethylsilyl-1--o-(arabinofurano syl)uracil phosphoramidate ProTides (2010) *Antiviral Chemistry & Chemotherapy* 20:153-160.

Murakami et al., Mechanism of Activation of PSI-7851and Its Diastereoisomer PSI-7977 (2010) *Journal of Biological Chemistry* 285:34337-34347.

Murakami et al., Mechanism of Activation of -D-2'-Deoxy-2'-Fiuoro-2'-C-Methylcytidine and Inhibition of Hepatitis C Virus NSSB RNA polymerase (2007) *Antimicrobial Agents and Chemotherapy* 51:503-509.

Olsen et al., A 7-Deaza-Adenosine Analog Is a Potent and Selective Inhibitor of Hepatitis C Virus Replication with Excellent Pharmacokinetic Properties (2004) *Antimicrobial Agents and Chemotherapy* 28:3944-3953.

Perrone et al., Application of the Phosphoramidate ProTide Approach to 4'-Azidouridine Confers Sub-micromolar Potency versus Hepatitis C Virus on an Inactive Nucleoside (2007) *Journal of Medicinal Chemistry* 50:1840-1849.

Prakash et al., Synthesis and Evaluation of 5-Acyl-2-thioethyl Esters of Modified Nucleoside 5'Monophosphates as Inhibitors of Hepatitis C Virus RNA Replication (2005) *J. Med. Chem.* 48:1199-1210.

Saboulard et al., Characterization of the Activation Pathway of Phosphoramidate Triester Prodrugs of Stavudine and Zidovudine (2009) *Molecular Pharmacology* 56:693-704.

Shen et al., Design and synthesis of vidarabine prodrugs as antiviral agents (2009) *Bioorganic & Medicinal Chemistry Letters* 19:792-796.

Sofia et al., Discovery of a 6-o-2'-Deoxy-2'-a-fluoro-2'-6-C-methyluridine Nucleotide Prodrug (PSI-7977) for the Treatment of Hepatitis CVirus (2010) *Journal of Medicinal Chemistry* 53:7202-7218.

Stein et al., Phosphorylation of Nucleoside Analog Antiretrovirals: A Review for Clinicians (2001) *Pharmacotherapy* 21:11-34.

Tomassini et al., Inhibitory Effect of 2'-Substituted Nucleosides on Hepatitis C Virus Replication Correlates with Metabolic Properties in Replicon Cells (2005) *Antimicrobial Agents and Chemotherapy* 49:2050-2058.

Cahard et al., Aryloxy Phosphoramidate Triesters as Pro-Tides (2004) *Mini-Reviews in Medicinal Chemistry* 4:371-381.

Kakefuda et al., Nucleosides and nucleotides. 120. Stereoselective radical deoxygenation of tert—alcohols in the sugar moiety of nucleosides: synthesis of 2',3'-dideoxy-2'-C-methyl- -2'-C-ethynyl--d- threo-pentofuranosyl pyrimidines and adenine as potential antiviral and antitumor agents (1993) *Tetrahedron* 49:8513-8528.

Kawana et al., The deoxygenations of tosylated adenosine derivatives with Grignard reagents (1986) *Nucleic Acids Symp Ser.* 17:37-40.

Kawana et al., The Synthesis of C-Methyl Branched-Chain Deoxy Sugar Nucleosides by the Deoxygenative Methylation of 0-Tosylated Adenosines with Grignard Reagents (1988) *Bull. Chem. Soc. Jpn.* 61:2437-2442.

Madela et al., Progress in the development of anti-hepatitis C virus nucleoside and nucleotide prodrugs (2012) *Future Med. Chem.* 4:625-650.

Pierra et al., Synthesis of 2'-C-Methylcytidine and 2'-C-Methyluridine Derivatives Modified in the 3'-Position as Potential Antiviral Agents (2006) *Collection of Czechoslovak Chemical Communications* 71:991-1010.

Tong et al., Nucleosides of thioguanine and other 2-amino-6-substituted purines from 2-acetamido-5-chloropurine (1967) *J Org Chem.* 32:859-62.

Vernachio et al., INX-08189, a Phosphoramidate Prodrug of 6-0-Methyi-2'-C-Methyl Guanosine, Is a Potent Inhibitor of Hepatitis C Virus Replication with Excellent Pharmacokinetic and Pharmacodynamic Properties (2011) Antimicrobial Agents and Chemotherapy 55:1843-1851.

Dang, Q., et al., "Syntheses of Nucleosides with 2'-Spirolactam and 2'-Spiropyrroliine Moieties as Potential Inhibitors of Hepatitis C Virus NS5B Polymerase", Tetrahedron Letters, vol. 55, pp. 3813-3816 (2014).

(56) References Cited

OTHER PUBLICATIONS

Du, J., et al., "Use of 2'-Spirocyclic Ethers in HCV Nucleoside Design", Journal of Medicinal Chemistry, vol. 57, pp. 1826-1835 (2014).

Jonckers, T., et al., "Nucleotide Prodrugs of 2'-Dooxy-2'-Spirooxetane Ribonucleosides as Novel Inhibitors of the HCV NS5 Polymerase", Journal of Medicinal Chemistry, vol. 57, pp. 1836-1844 (2014).

Zheng, Y., et al., "The Use of Spirocyclic Scaffolds in Drug Discovery", Bioorganic & Medicinal Chemistry Letters, vol. 24, pp. 3673-3682 (2014).

International search report dated Jul. 9 2013, for corresponding international application PCT/EP2013/060704.

European search report dated Aug. 13, 2012, for corresponding European application 12169425.1.

Jonckers, T., et al., "Discovery of 1-((2R,4aR,6R,7R,7aR)-2-Isopropoxy-2-oxidodihydro-4H,6H-spiro[furo[3,2-d][1,3,2]dioxaphosphinine-7,2'-oxetan]-6-yl)pyrimidine-2,4(1H,3H)-dione (JNJ-54257099), a 3'-5'-Cyclic Phosphate Ester Prodrug of 2'-Deoxy-2'-Spirooxetane Uridine Triphosphate Useful for HCV Inhibition", J. of Medicinal Chemistry, vol. 59, pp. 5790-5798 (2016).

Lohmann et al., "Replication of Subgenomic Hepatitis C Virus RNAs in a Hepatoma Cell Line", Science, 285, pp. 110-113 (1999).

Kreiger et al., "Enhancement of Hepatitis C Virus RNA Replication by Cell Culture-Adaptive Mutations", Journal of Virology 75, pp. 4614-4624 (2001).

Inoue et al., "Evaluation of a Cyclophilin Inhibitor in Hepatitis C Virus-Infected Chimeric Mice in Vivo", Hepatology, 45(4), pp. 921-928 (2007).

Taneto et al., "Near Completely Humanized Liver in Mice Shows Human-Type Metabolic Responses to Drugs", American Journal of Pathology, vol. 165, No. 3, pp. 901-912 (2004).

Versteeg et al., "Synthesis, structure, and sugar dynamics of a 2'-spiroisoxazolidine thymidine analog", Tetrahedron, vol. 66, pp. 8145-8150 (2010).

Babu et al., "2'-Spiro ribo-and arabinonucleosides: synthesis, molecular modelling and incorporation into oligodeoxynucleotides", Organic and Biomolecular Chemistry, vol. 1 (20), pp. 3514-3526 (2003).

* cited by examiner

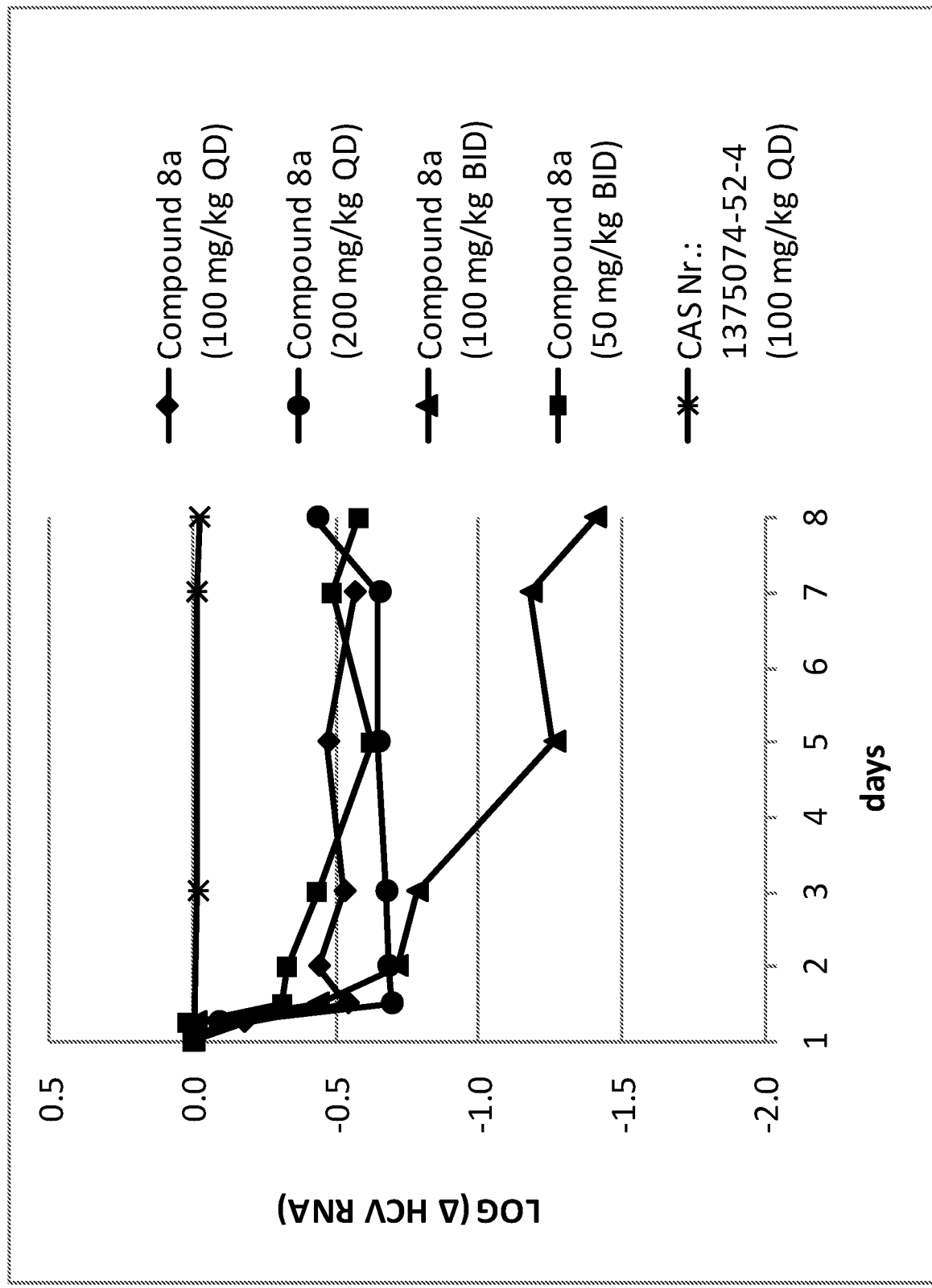

URACYL SPIROOXETANE NUCLEOSIDES

This application is a continuation of U.S. application Ser. No. 16/212,554 filed on Dec. 6, 2018, pending, which is a continuation of U.S. application Ser. No. 16/044,262 filed on Jul. 24, 2018, now abandoned, which is a continuation of U.S. application Ser. No. 15/809,730 filed on Nov. 10, 2017, now U.S. Pat. No. 10,040,814 issued on Aug. 7, 2018, which is a continuation of U.S. application Ser. No. 15/423,985 filed on Feb. 3, 2017, now U.S. Pat. No. 9,845,336 issued on Dec. 19, 2017, which is a continuation of U.S. application Ser. No. 15/238,553 filed on Aug. 16, 2016, now abandoned, which is a continuation application of U.S. application Ser. No. 14/403,587 filed on Nov. 25, 2014, now U.S. Pat. No. 9,422,323 issued on Aug. 23, 2016, which is a 35 U.S.C. § 371 nationalization of PCT application PCT/EP2013/060704 filed on May 24, 2013, which claims priority to European patent application EP 12169425.1 filed on May 25, 2012, all of which are incorporated herein by reference.

BACKGROUND OF THE INVENTION

This invention relates to spirooxetane nucleosides and nucleotides that are inhibitors of the hepatitis C virus (HCV).

HCV is a single stranded, positive-sense RNA virus belonging to the Flaviviridae family of viruses in the hepacivirus genus. The NS5B region of the RNA polygene encodes a RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations. There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapy is based on (pegylated) interferon-alpha (IFN-α) in combination with ribavirin. This combination therapy yields a sustained virologic response in more than 40% of patients infected by genotype 1 HCV and about 80% of those infected by genotypes 2 and 3. Beside the limited efficacy against HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Recently, therapy possibilities have extended towards the combination of a HCV protease inhibitor (e.g. Telaprevir or boceprevir) and (pegylated) interferon-alpha (IFN-α)/ribavirin.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RdRp is essential for replication of the single-stranded, positive sense, HCV RNA genome. This enzyme has elicited significant interest among medicinal chemists. Both nucleoside and non-nucleoside inhibitors of NS5B are known. Nucleoside inhibitors can act as a chain terminator or as a competitive inhibitor, or as both. In order to be active, nucleoside inhibitors have to be taken up by the cell and converted in vivo to a triphosphate. This conversion to the triphosphate is commonly mediated by cellular kinases, which imparts additional structural requirements on a potential nucleoside polymerase inhibitor. In addition this limits the direct evaluation of nucleosides as inhibitors of HCV replication to cell-based assays capable of in situ phosphorylation.

Several attempts have been made to develop nucleosides as inhibitors of HCV RdRp, but while a handful of compounds have progressed into clinical development, none have proceeded to registration. Amongst the problems which HCV-targeted nucleosides have encountered to date are toxicity, mutagenicity, lack of selectivity, poor efficacy, poor bioavailability, sub-optimal dosage regimes and ensuing high pill burden and cost of goods.

Spirooxetane nucleosides, in particular 1-(8-hydroxy-7-(hydroxy-methyl)-1,6-dioxaspiro[3.4]octan-5-yl)pyrimidine-2,4-dione derivatives and their use as HCV inhibitors are known from WO2010/130726, and WO2012/062869, including CAS-1375074-52-4.

There is a need for HCV inhibitors that may overcome at least one of the disadvantages of current HCV therapy such as side effects, limited efficacy, the emerging of resistance, and compliance failures, or improve the sustained viral response.

The present invention concerns a group of HCV-inhibiting uracyl spirooxetane derivatives with useful properties regarding one or more of the following parameters: antiviral efficacy towards at least one of the following genotypes 1a, 1b, 2a, 2b, 3,4 and 6, favorable profile of resistance development, lack of toxicity and genotoxicity, favorable pharmacokinetics and pharmacodynamics and ease of formulation and administration.

DESCRIPTION OF THE INVENTION

In one aspect the present invention provides compounds that can be represented by the formula I:

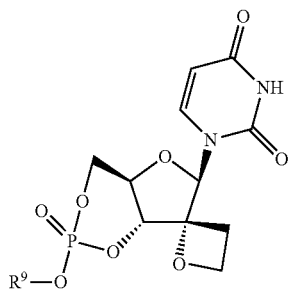

(I)

including any possible stereoisomer thereof, wherein:

$R^9$ is $C_1$-$C_6$alkyl, phenyl, $C_3$-$C_7$cycloalkyl or $C_1$-$C_3$alkyl substituted with 1, 2 or 3 substituents each independently selected from phenyl, naphthyl, $C_3$-$C_6$cycloalkyl, hydroxy, or $C_1$-$C_6$alkoxy;

or a pharmaceutically acceptable salt or solvate thereof.

Of particular interest are compounds of formula I or subgroups thereof as defined herein, that have a structure according to formula Ia:

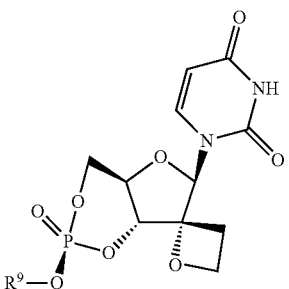

(Ia)

In one embodiment of the present invention, $R^9$ is $C_1$-$C_6$alkyl, phenyl, $C_3$-$C_7$cycloalkyl or $C_1$-$C_3$alkyl substituted with 1 substituent selected from phenyl, $C_3$-$C_6$cycloalkyl, hydroxy, or $C_1$-$C_6$alkoxy. In another embodiment of the present invention, $R^9$ in Formula I or Ia is $C_1$-$C_6$alkyl or $C_1$-$C_2$alkyl substituted with phenyl $C_1$-$C_2$alkoxy or $C_3$-$C_6$cycloalkyl. In a more preferred embodiment, $R^9$ is $C_2$-$C_4$alkyl and in a most preferred embodiment, $R^9$ is i-propyl.

A preferred embodiment according to the invention is a compound according to formula Ib:

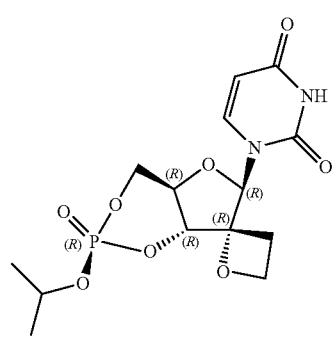

(Ib)

including any pharmaceutically acceptable salt or solvate thereof and the use of compound (V) in the synthesis of a compound according to Formula I, Ia or Ib.

The invention further relates to a compound of formula V:

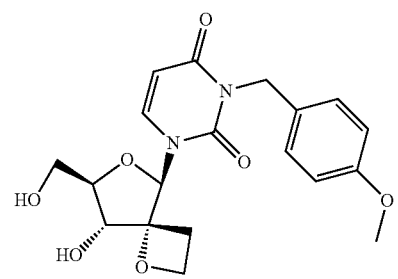

(V)

including any pharmaceutically acceptable salt or solvate thereof and the use of compound (V) in the synthesis of a compound according to Formula I, Ia or Ib.

In addition, the invention relates to a compound of formula VI:

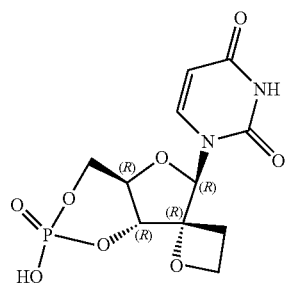

(VI)

including any stereochemical form and/or pharmaceutically acceptable salt or solvate thereof.

Additionally, the invention relates to a pharmaceutical composition comprising a compound according to Formula I, Ia or Ib, and a pharmaceutically acceptable carrier. The invention also relates to a product containing (a) a compound of formula I, Ia or Ib a, and (b) another HCV inhibitor, as a combined preparation for simultaneous, separate or sequential use in the treatment of HCV infections Yet another aspect of the invention relates to a compound according to Formula I, Ia or Ib or a pharmaceutical composition according to the present invention for use as a medicament, preferably for use in the prevention or treatment of an HCV infection in a mammal.

In a further aspect, the invention provides a compound of formula I Ia or Ib or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

Of particular interest is compound 8a mentioned in the section "Examples" as well as the pharmaceutically acceptable acid addition salts of this compound.

The compounds of formula I have several centers of chirality, in particular at the carbon atoms 1', 2', 3', and 4'. Although the stereochemistry at these carbon atoms is fixed, the compounds may display at least 75%, preferably at least 90%, such as in excess of 95%, or of 98%, enantiomeric purity at each of the chiral centers.

The phosphorus center can be present as $R_P$ or $S_P$, or a mixture of such stereoisomers, including racemates. Diastereoisomers resulting from the chiral phosphorus center and a chiral carbon atom may exist as well.

The compounds of formula I are represented as a defined stereoisomer, except for the stereoisomerism at the phosphorous atom. The absolute configuration of such compounds can be determined using art-known methods such as, for example, X-ray diffraction or NMR and/or implication from starting materials of known stereochemistry. Pharmaceutical compositions in accordance with the invention will preferably comprise stereoisomerically pure forms of the indicated stereoisomer of the particular compound of formula I.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%, or of 98% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary layers. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography.

The pharmaceutically acceptable addition salts comprise the therapeutically active non-toxic acid and base addition salt forms of the compounds of formula I. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, palmoic and the like acids. Conversely said salt forms can be converted by treatment with an appropriate base into the free base form.

The compounds of formula I containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in their tautomeric form. For example, tautomeric forms of amide (—C(=O)—NH—) groups are iminoalcohols (—C(OH)=N—), which can become stabilized in rings with aromatic character. The uridine base is an example of such a form. Such forms, although not explicitly indicated in the structural formulae represented herein, are intended to be included within the scope of the present invention.

SHORT DESCRIPTION OF THE FIGURE

FIG. 1: In vivo efficacy of compound 8a and CAS-1375074-52-4 as determined in a humanized hepatocyte mouse model.

DEFINITIONS

As used herein "$C_1$-$C_n$alkyl" as a group or part of a group defines saturated straight or branched chain hydrocarbon radicals having from 1 to n carbon atoms. Accordingly, "$C_1$-$C_4$alkyl" as a group or part of a group defines saturated straight or branched chain hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl.

'$C_1$-$C_n$alkoxy' means a radical —O—$C_1$-$C_n$alkyl wherein $C_1$-$C_n$alkyl is as defined above. Accordingly, '$C_1$-$C_6$alkoxy' means a radical —O—$C_1$-$C_6$alkyl wherein $C_1$-$C_6$alkyl is as defined above. Examples of $C_1$-$C_6$alkoxy are methoxy, ethoxy, n-propoxy, or isopropoxy. Of interest is '$C_1$-$C_2$alkoxy', encompassing methoxy and ethoxy.

"$C_3$-$C_6$cycloalkyl" includes cyclopropyl, cyclobutyl, cyclopentyl, and cyclohexyl.

In one embodiment, the term "phenyl-$C_1$-$C_6$alkyl" is benzyl.

As used herein, the term '(=O)' or 'oxo' forms a carbonyl moiety when attached to a carbon atom. It should be noted that an atom can only be substituted with an oxo group when the valency of that atom so permits.

The term "monophosphate, diphosphate or triphosphate ester" refers to groups:

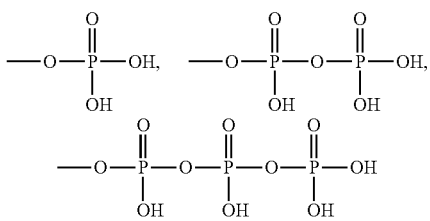

Where the position of a radical on a molecular moiety is not specified (for example a substituent on phenyl) or is represented by a floating bond, such radical may be positioned on any atom of such a moiety, as long as the resulting structure is chemically stable. When any variable is present more than once in the molecule, each definition is independent.

Whenever used herein, the term 'compounds of formula I', or 'the present compounds' or similar terms, it is meant to include the compounds of Formula I, Ia and Ib, including the possible stereochemically isomeric forms, and their pharmaceutically acceptable salts and solvates.

The present invention also includes isotope-labeled compounds of formula I or any subgroup of formula I, wherein one or more of the atoms is replaced by an isotope that differs from the one(s) typically found in nature. Examples of such isotopes include isotopes of hydrogen, such as $^2H$ and $^3H$; carbon, such as $_{11}$-C, $^{13}C$ and $^{14}C$; nitrogen, such as $^{13}N$ and $^{15}N$; oxygen, such as $^{15}O$ and $^{18}O$; phosphorus, such as $^{31}P$ and $^{32}P$, sulphur, such as $^{35}S$; fluorine, such as $^{18}F$; chlorine, such as $^{36}Cl$; bromine such as $^{75}Br$, $^{76}Br$, $^{77}Br$ and $^{82}Br$; and iodine, such as $^{123}I$, $^{124}I$, $^{125}I$ and $^{131}I$. Isotope-labeled compounds of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3H$ or $^{14}C$ is incorporated. For radio-imaging applications, a positron emitting isotope such as $^{11}C$, $^{18}F$, $^{13}N$ or $^{15}O$ will be useful. The incorporation of deuterium may provide greater metabolic stability, resulting in, e.g. an increased in vivo half life of the compound or reduced dosage requirements.

General Synthetic Procedures

The following schemes are just meant to be illustrative and are by no means limiting the scope.

The starting material 1-[(4R,5R,7R,8R)-8-hydroxy-7-(hydroxymethyl)-1,6-dioxa-spiro[3.4]octan-5-yl]pyrimidine-2,4(1H,3H)-dione (1) can be prepared as exemplified in WO2010/130726. Compound (1) is converted into compounds of the present invention via a p-methoxybenzyl protected derivative (4) as exemplified in the following Scheme 1.

Scheme 1

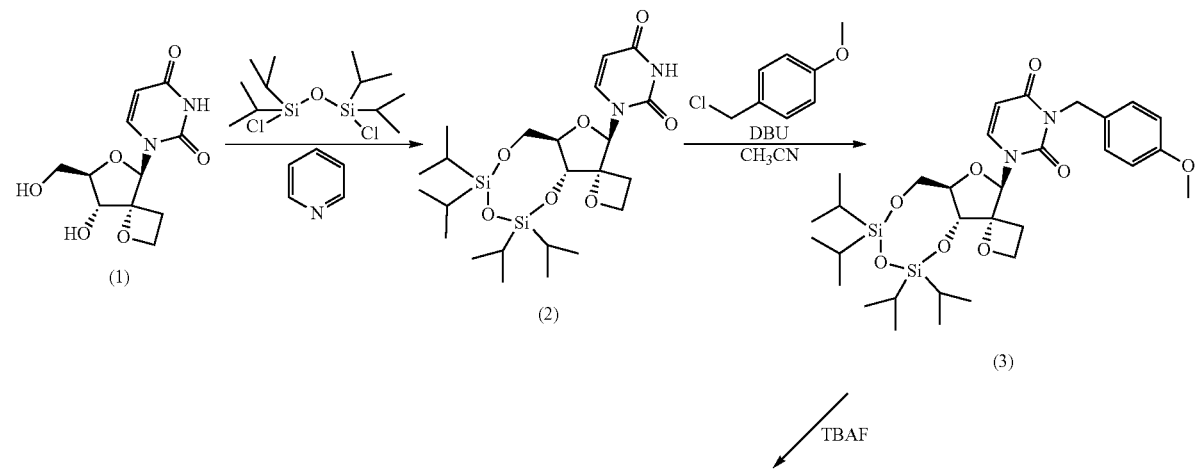

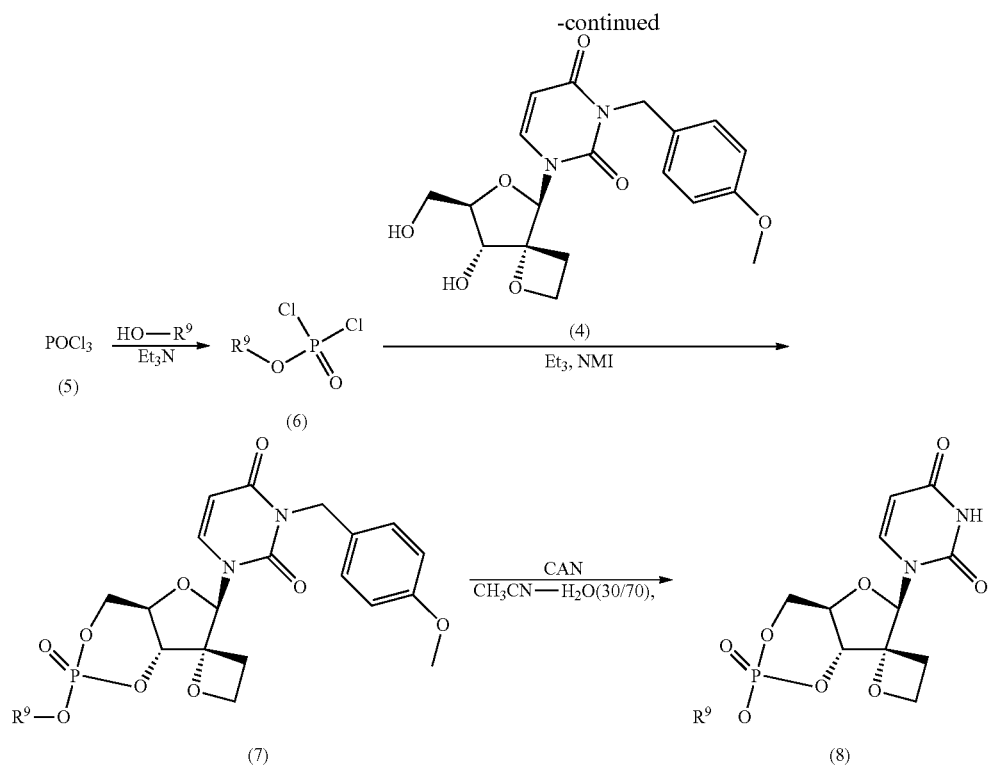

In Scheme 1, $R^9$ can be $C_1$-$C_6$alkyl, phenyl, naphtyl, $C_3$-$C_7$cycloalkyl or $C_1$-$C_3$alkyl substituted with 1, 2 or 3 substituents each independently selected from phenyl, $C_3$-$C_6$cycloalkyl, hydroxy, or $C_1$-$C_6$alkoxy, preferably $R^9$ is $C_1$-$C_6$alkyl or $C_1$-$C_2$alkyl substituted with phenyl, $C_1$-$C_2$alkoxy or $C_3$-$C_6$cycloalkyl, even more preferably $R^9$ is $C_2$-$C_4$alkyl and most preferably $R^9$ is i-propyl.

In a further aspect, the present invention concerns a pharmaceutical composition comprising a therapeutically effective amount of a compound of formula I as specified herein, and a pharmaceutically acceptable carrier. Said composition may contain from 1% to 50%, or from 10% to 40% of a compound of formula I and the remainder of the composition is the said carrier. A therapeutically effective amount in this context is an amount sufficient to act in a prophylactic way against HCV infection, to inhibit HCV, to stabilize or to reduce HCV infection, in infected subjects or subjects being at risk of becoming infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

The compounds of formula I or of any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and/or prophylaxis of HCV infection or diseases associated with HCV. The latter include progressive liver fibrosis, inflammation and necrosis leading to cirrhosis, end-stage liver disease, and HCC. The compounds of this invention moreover are believed to be active against mutated strains of HCV and show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I, including any possible stereoisomers, the pharmaceutically acceptable addition salts or solvates thereof, are useful in the treatment of warm-blooded animals, in particular humans, infected with HCV, and in the prophylaxis of HCV infections. The compounds of the present invention may therefore be used as a medicine, in particular as an anti-HCV or a HCV-inhibiting medicine. The present invention also relates to the use of the present compounds in the manufacture of a medicament for the treatment or the prevention of HCV infection. In a further aspect, the present invention relates to a method of treating a warm-blooded animal, in particular human, infected by HCV, or being at risk of becoming infected by HCV, said method comprising the administration of an anti-HCV effective amount of a compound of formula I, as specified herein. Said use as a medicine or method of treatment comprises the systemic administration to HCV-infected subjects or to subjects susceptible to HCV infection of an amount effective to combat the conditions associated with HCV infection.

In general it is contemplated that an antiviral effective daily amount would be from about 1 to about 30 mg/kg, or about 2 to about 25 mg/kg, or about 5 to about 15 mg/kg, or about 8 to about 12 mg/kg body weight. Average daily doses can be obtained by multiplying these daily amounts by about 70. It may be appropriate to administer the required dose as two, three, four or more sub-doses at appropriate intervals throughout the day. Said sub-doses may be formulated as unit dosage forms, for example, containing about 1 to about 2000 mg, or about 50 to about 1500 mg, or about 100 to about 1000 mg, or about 150 to about 600 mg, or about 100 to about 400 mg of active ingredient per unit dosage form.

As used herein the term "about" has the meaning known to the person skilled in the art. In certain embodiments the term "about" may be left out and the exact amount is meant. In other embodiments the term "about" means that the numerical following the term "about" is in the range of ±15%, or of ±10%, or of ±5%, or of ±1%, of said numerical value.

EXAMPLES

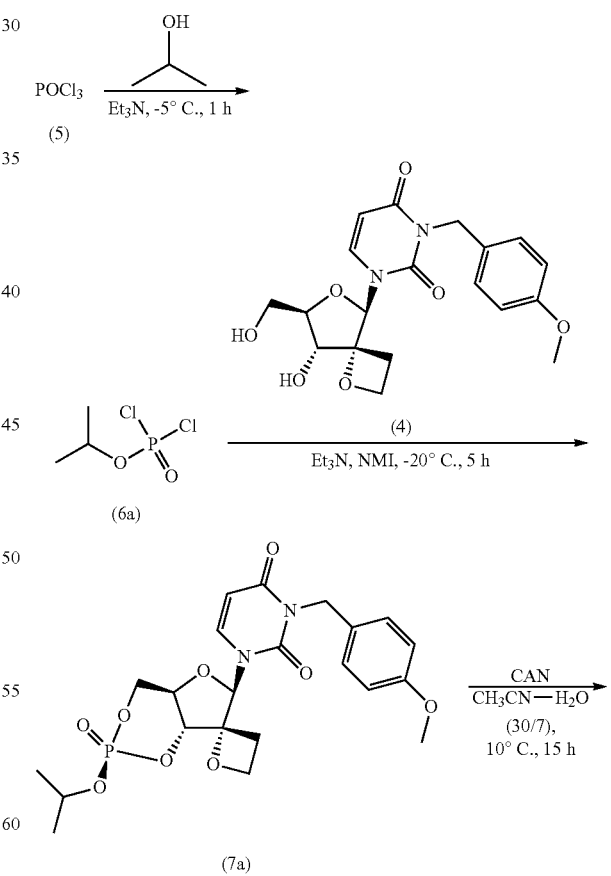

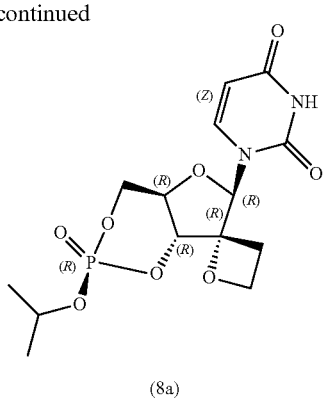

(8a)

Synthesis of Compound (2)

Compound (2) can be prepared by dissolving compound (1) in pyridine and adding 1,3-dichloro-1,1,3,3-tetraisopropyldisiloxane. The reaction is stirred at room temperature until complete. The solvent is removed and the product redissolved in $CH_2Cl_2$ and washed with saturated $NaHCO_3$ solution. Drying on $MgSO_4$ and removal of the solvent gives compound (2).

Synthesis of Compound (3)

Compound (3) is prepared by reacting compound (2) with p-methoxybenzylchloride in the presence of DBU as the base in $CH_3CN$.

Synthesis of Compound (4)

Compound (4) is prepared by cleavage of the bis-silyl protecting group in compound (3) using TBAF as the fluoride source.

Synthesis of Compound (6a)

A solution of isopropyl alcohol (3.86 mL, 0.05 mol) and triethylamine (6.983 mL, 0.05 mol) in dichloromethane (50 mL) was added to a stirred solution of $POCl_3$ (5) (5.0 mL, 0.0551 mol) in DCM (50 mL) dropwise over a period of 25 min at −5° C. After the mixture stirred for 1 h, the solvent was evaporated, and the residue was suspended in ether (100 mL). The triethylamine hydrochloride salt was filtered and washed with ether (20 mL). The filtrate was concentrated, and the residue was distilled to give the (6) as a colorless liquid (6.1 g, 69% yield).

Synthesis of Compound (7a)

To a stirred suspension of (4) (2.0 g, 5.13 mmol) in dichloromethane (50 mL) was added triethylamine (2.07 g, 20.46 mmol) at room temperature. The reaction mixture was cooled to −20° C., and then (6a) (1.2 g, 6.78 mmol) was added dropwise over a period of 10 min. The mixture was stirred at this temperature for 15 min and then NMI was added (0.84 g, 10.23 mmol), dropwise over a period of 15 min. The mixture was stirred at −15° C. for 1 h and then slowly warmed to room temperature in 20 h. The solvent was evaporated, the mixture was concentrated and purified by column chromatography using petroleum ether/EtOAc (10:1 to 5:1 as a gradient) to give (7a) as white solid (0.8 g, 32% yield).

Synthesis of Compound (8a)

To a solution of (7a) in $CH_3CN$ (30 mL) and $H_2O$ (7 mL) was add CAN portion wise below 20° C. The mixture was stirred at 15-20° C. for 5 h under $N_2$. $Na_2SO_3$ (370 mL) was added dropwise into the reaction mixture below 15° C., and then $Na_2CO_3$ (370 mL) was added. The mixture was filtered and the filtrate was extracted with $CH_2Cl_2$ (100 mL*3). The organic layer was dried and concentrated to give the residue. The residue was purified by column chromatography to give the target compound (8a) as white solid. (Yield: 55%)

$^1$H NMR (400 MHz, CHLOROFORM-d) δ ppm 1.45 (dd, J=7.53, 6.27 Hz, 6H), 2.65-2.84 (m, 2H), 3.98 (td, J=10.29, 4.77 Hz, 1H), 4.27 (t, J=9.66 Hz, 1H), 4.43 (ddd, J=8.91, 5.77, 5.65 Hz, 1H), 4.49-4.61 (m, 1H), 4.65 (td, J=7.78, 5.77 Hz, 1H), 4.73 (d, J=7.78 Hz, 1H), 4.87 (dq, J=12.74, 6.30 Hz, 1H), 5.55 (br. s., 1H), 5.82 (d, J=8.03 Hz, 1H), 7.20 (d, J=8.03 Hz, 1H), 8.78 (br. s., 1H); $^{31}$P NMR (CHLOROFORM-d) δ ppm −7.13; LC-MS: 375 (M+1)+

Scheme 3
Synthesis of compound (VI)

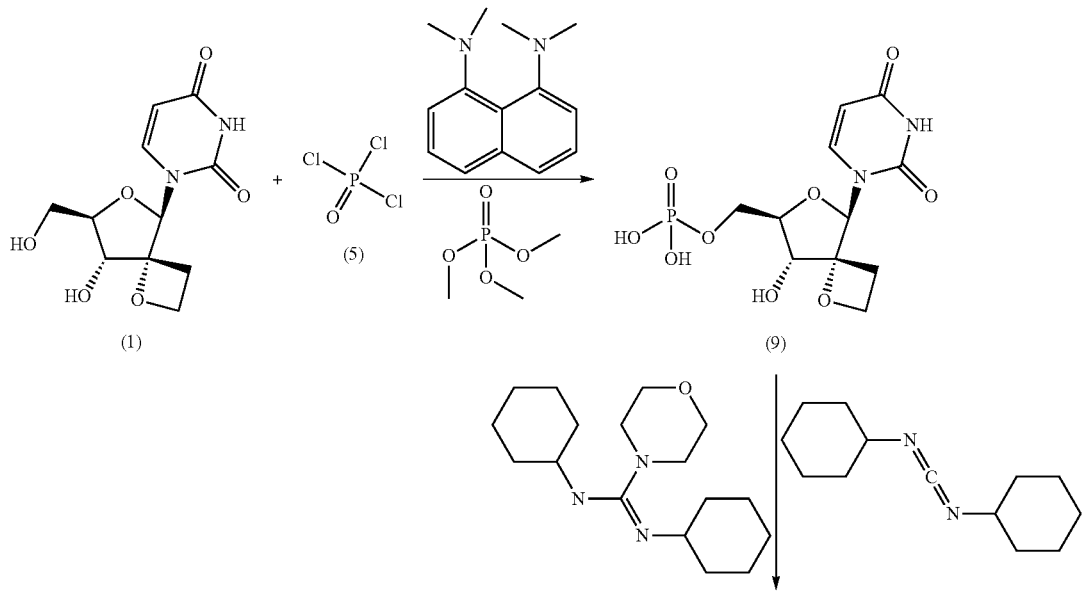

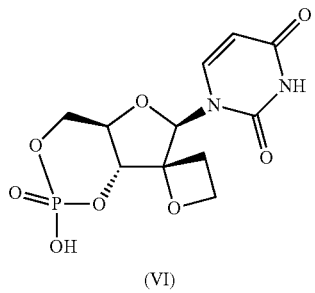

(VI)

Step 1: Synthesis of Ccompound (9)

Compound (1), CAS 1255860-33-3 (1200 mg, 4.33 mmol) and 1,8-bis(dimethyl-amino)naphthalene (3707 mg, 17.3 mmol) were dissolved in 24.3 mL of trimethylphosphate. The solution was cooled to 0° C. Compound (5) (1.21 mL, 12.98 mmol) was added, and the mixture was stirred well maintaining the temperature at 0° C. for 5 hours. The reaction was quenched by addition of 120 mL of tetraethyl-ammonium bromide solution (1M) and extracted with $CH_2Cl_2$ (2×80 mL). Purification was done by preparative HPLC (Stationary phase: RP XBridge Prep C18 OBD-10 μm, 30×150 mm, mobile phase: 0.25% $NH_4HCO_3$ solution in water, $CH_3CN$), yielding two fractions. The purest fraction was dissolved in water (15 mL) and passed through a manually packed Dowex ($H^+$) column by elution with water. The end of the elution was determined by checking UV absorbance of eluting fractions. Combined fractions were frozen at −78° C. and lyophilized. Compound (9) was obtained as a white fluffy solid (303 mg, (0.86 mmol, 20% yield), which was used immediately in the following reaction.

Step 2: Preparation of Compound (VI)

Compound (9) (303 mg, 0.86 mmol) was dissolved in 8 mL water and to this solution was added N,N'-Dicyclohexyl-4-morpholine carboxamidine (253.8 mg, 0.86 mmol) dissolved in pyridine (8.4 mL). The mixture was kept for 5 minutes and then evaporated to dryness, dried overnight in vacuo overnight at 37° C. The residu was dissolved in pyridine (80 mL). This solution was added dropwise to vigorously stirred DCC (892.6 mg, 4.326 mmol) in pyridine (80 mL) at reflux temperature. The solution was kept refluxing for 1.5 h during which some turbidity was observed in the solution. The reaction mixture was cooled and evaporated to dryness. Diethylether (50 mL) and water (50 mL) were added to the solid residu. N'N-dicyclohexylurea was filtered off, and the aqueous fraction was purified by preparative HPLC (Stationary phase: RP XBridge Prep C18 OBD-10 μm, 30×150 mm, mobile phase: 0.25% $NH_4HCO_3$ solution in water, $CH_3CN$), yielding a white solid which was dried overnight in vacuo at 38° C. (185 mg, 0.56 mmol, 65% yield). LC-MS: $(M+H)^+$: 333.

$^1$H NMR (400 MHz, DMSO-$d_6$) δ ppm 2.44-2.59 (m, 2H) signal falls under DMSO signal, 3.51 (td, J=9.90, 5.50 Hz, 1H), 3.95-4.11 (m, 2H), 4.16 (d, J=10.34 Hz, 1H), 4.25-4.40 (m, 2H), 5.65 (d, J=8.14 Hz, 1H), 5.93 (br. s., 1H), 7.46 (d, J=7.92 Hz, 1H), 2H's not observed Biological Examples Replicon Assays The compounds of formula I were examined for activity in the inhibition of HCV-RNA replication in a cellular assay. The assay was used to demonstrate that the compounds of formula I inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

Replicon Assay (A)

In essence, the method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an internal ribosome entry site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV genotype 1b.

Continued culture of the replicon cells in the presence of G418 ($neo^R$) is dependent on the replication of the HCV-RNA. The stably transfected replicon cells that express HCV-RNA, which replicates autonomously and to high levels, encoding inter alia luciferase, were used for screening the antiviral compounds.

The replicon cells were plated in 384-well plates in the presence of the test and control compounds which were added in various concentrations. Following an incubation of three days, HCV replication was measured by assaying luciferase activity (using standard luciferase assay substrates and reagents and a Perkin Elmer ViewLuxi™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease the level of detected luciferase activity by 50%, or more specifically, the ability of the genetically linked HCV replicon RNA to replicate.

Results (A)

Table 1 shows the replicon results ($EC_{50}$, replicon) and cytotoxicity results ($CC_{50}$ (μM) (Huh-7)) obtained for the compound of the examples given above.

TABLE 1

| Compound number | $EC_{50}$ (μM) (HCV) | $CC_{50}$ (μM) (Huh-7) |
|---|---|---|
| 8a | 0.13 (n = 4) | >100 |

Replicon Assays (B)

Further replicon assays were performed with compound 8a of which the protocols and results are disclosed below.

Assay 1

The anti-HCV activity of compound 8a was tested in cell culture with replicon cells generated using reagents from the Bartenschlager laboratory (the HCV 1b bicistronic subgenomic luciferase reporter replicon clone ET). The protocol included a 3-day incubation of 2500 replicon cells in a 384-well format in a nine-point 1:4 dilution series of the compound. Dose response curves were generated based on the firefly luciferase read-out. In a variation of this assay, a 3 day incubation of 3000 cells in a 96-well format in a nine-point dilution series was followed by qRT-PCR Taqman detection of HCV genome, and normalized to the cellular transcript, RPL13 (of the ribosomal subunit RPL13 gene) as a control for compound inhibition of cellular transcription.

Assay 2

The anti-HCV activity of compound 8a was tested in cell culture with replicon cells generated using reagents from the Bartenschlager laboratory (the HCV 1b bicistronic subgenomic luciferase reporter replicon clone ET or Huh-Luc-Neo). The protocol included a 3-day incubation of $2 \times 10^4$ replicon cells in a 96-well format in a six-point 1:5 dilution series of the compound. Dose response curves were generated based on the luciferase read-out.

Assay 3

The anti-HCV activity of compound 8a was tested in cell culture with replicon cells generated using reagents from the Bartenschlager laboratory (the HCV 1b bicistronic subgenomic luciferase reporter replicon clone ET or Huh-Luc-Neo). The protocol included either a 3-day incubation of $8 \times 10^3$ cells or $2 \times 10^4$ cells in a 96-well format in an eight-point 1:5 dilution series of the compound. Dose response curves were generated based on the luciferase read-out.

Results

Table 2 shows the average replicon results ($EC_{50}$, replicon) obtained for compound 8a following assays as given above.

TABLE 2

| Assay | Average $EC_{50}$ value (8a): |
|---|---|
| 1 | 57 µM (n = 8) |
| 2 | 17.5 µM (n = 4) |
| 3 | >100 µM (n = 1) |

Primary Human Hepatocyte In Vitro Assay

The anti-HCV activity of compound 8a was determined in an in vitro primary human hepatocyte assay. Protocols and results are disclosed below.

Protocol

Hepatocyte Isolation and Culture

Primary human hepatocytes (PHH) were prepared from patients undergoing partial hepatectomy for metastases or benign tumors. Fresh human hepatocytes were isolated from encapsulated liver fragments using a modification of the two-step collagenase digestion method. Briefly, encapsulated liver tissue was placed in a custom-made perfusion apparatus and hepatic vessels were cannulated with tubing attached multichannel manifold. The liver fragment was initially perfused for 20 min with a prewarmed (37° C.) calcium-free buffer supplemented with ethylene glycol tetraacetic acid (EGTA) followed by perfusion with a prewarmed (37° C.) buffer containing calcium ($CaCl_2$, $H_2O_2$) and collagenase 0.05% for 10 min. Then, liver fragment was gently shaken to free liver cells in Hepatocyte Wash Medium. Cellular suspension was filtered through a gauze-lined funnel. Cells were centrifuged at low speed centrifugation. The supernatant, containing damaged or dead hepatocytes, non parenchymal cells and debris was removed and pelleted hepatocytes were re-suspended in Hepatocyte Wash Medium. Viability and cell concentration were determined by trypan blue exclusion test.

Cells were resuspended in complete hepatocyte medium consisting of William's medium (Invitrogen) supplemented with 100 IU/L insulin (Novo Nordisk, France), and 10% heat inactivated fetal calf serum (Biowest, France), and seeded at a density $1.8 \times 10^6$ viable cells onto 6 well plates that had been precoated with a type I collagen from calf skin (Sigma-Aldrich, France) The medium was replaced 16-20 hours later with fresh complete hepatocyte medium supplemented with hydrocortisone hemisuccinate (SERB, Paris, France), and cells were left in this medium until HCV inoculation. The cultures were maintained at 37° C. in a humidified 5% CO2 atmosphere.

The PHHs were inoculated 3 days after seeding. JFH1-HCVcc stocks were used to inoculate PHHs for 12 hours, at a multiplicity of infection (MOI) of 0.1 ffu per cell. After a 12-hours incubation at 37° C., the inoculum was removed, and monolayers were washed 3 times with phosphate-buffered saline and incubated in complete hepatocyte medium containing 0.1% dimethylsufoxide as carrier control, 100 IU/ml of IFNalpha as negative control or else increasing concentrations of compound 8a. The cultures then were maintained during 3 days.

Quantitation of HCV RNA

Total RNA was prepared from cultured cells or from filtered culture supernatants using the RNeasy or Qiamp viral RNA minikit respectively (Qiagen SA, Courtaboeuf, France) according to the manufacturer's recommendations. HCV RNA was quantified in cells and culture supernatants using a strand-specific reverse real-time PCR technique described previously (Carrière M and al 2007):

Reverse transcription was performed using primers described previously located in the 50 NCR region of HCV genome, tag-RC1 (5'-GGCCGTCATGGTGGC-GAATAAGTCTAGCCATGGCGTTAGTA-3') and RC21 (5'-CTCCCGGGGCACTCGCAAGC-3') for the negative and positive strands, respectively. After a denaturation step performed at 70° C. for 8 min, the RNA template was incubated at 4° C. for 5 min in the presence of 200 ng of tag-RC1 primer and 1.25 mM of each deoxynucleoside triphosphate (dNTP) (Promega, Charbonnieres, France) in a total volume of 12 µl.

Reverse transcription was carried out for 60 min at 60° C. in the presence of 20 U RNaseOut™ (Invitrogen, Cergy Pontoise, France) and 7.5 U Thermoscript™ reverse transcriptase (Invitrogen), in the buffer recommended by the manufacturer. An additional treatment was applied by adding 1 µl (2 U) RNaseH (Invitrogen) for 20 min at 37° C.

The first round of nested PCR was performed with 2 µl of the cDNA obtained in a total volume of 50 µl, containing 3 U Taq polymerase (Promega), 0.5 mM dNTP, and 0.5 µM RC1 (5'-GTCTAGCCATGGCGTTAGTA-3') and RC21 primers for positive-strand amplification, or Tag (5'-GGC-CGTCATGGTGGCGAATAA-3') and RC21 primers for negative strand amplification. The PCR protocol consisted of 18 cycles of denaturation (94° C. for 1 min), annealing (55° C. for 45 sec), and extension (72° C. for 2 min). The cDNA obtained was purified using the kit from Qiagen, according to the manufacturer's instructions.

The purified product was then subjected to real-time PCR. The reaction was carried out using the LightCycler 480 SYBR Green I Master (2× con) Kit (Roche, Grenoble, France), with LC480 instruments and technology (Roche Diagnostics). PCR amplifications were performed in a total volume of 10 µl, containing 5 µl of Sybrgreen I Master Mix (2×), and 25 ng of the 197R (5'-CTTTCGCGAC-CCAACACTAC-3') and 104 (5'-AGAGCCATAGTGGTCT-GCGG-3') primers. The PCR protocol consisted of one step of initial denaturation for 10 min at 94° C., followed by 40 cycles of denaturation (95° C. for 15 sec), annealing (57° C. for 5 sec), and extension (72° C. for 8 sec).

The quantitation of 28Sr RNA by specific RT-PCR was used as an internal standard to express the results of HCV positive or negative strands per µg of total hepatocyte RNA.

Specific primers for 28 S rRNA were designed using the Oligo6 software 5'-TTGAAAATCCGGGGGAGAG-3' (nt2717-2735) and 50-ACATTGTTCCAACATGCCAG-30 (nt 2816-2797). Reverse transcription was performed using AMV reverse transcriptase (Promega), and the PCR protocol consisted of one step of initial denaturation for 8 min at 95° C., followed by 40 cycles of denaturation (95° C. for 15 sec), annealing (54° C. for 5 sec), and extension (72° C. for 5 sec).

Results

Table 3 shows the anti-HCV activity of compound 8a as determined in the in vitro primary human hepatocyte assay described above. The numbers are expressed as $10^6$ HCV RNA copies/µg of total RNA. Results of two independent experiments (Exp 1 and Exp 2) are given. The data per experiment is the average of two measurements.

Table 3: Effect of compound 8a on positive strand HCV-RNA levels in primary human hepatocytes (expressed as $10^6$ HCV RNA copies/µg of total RNA).

TABLE 3

|  | Exp. 1 | Exp. 2 |
|---|---|---|
| No HCV | 0 | 0 |
| HCV control | 3.56 | 5.53 |
| IFNα (100 IU/mL) | 1.48 | 1.59 |
| 8a (0.195 µM) | 2.18 | 1.12 |
| 8a (0.78 µM) | 2.25 | 1.3 |
| 8a (3.12 µM) | 1.09 | 0.94 |
| 8a (12.5 µM) | 2.17 | 1.3 |
| 8a (50 µM) | 0.94 | 1.33 |

In Vivo Efficacy Assay

The in vivo efficacy of compound 8a and CAS-1375074-52-4 was determined in a humanized hepatocyte mouse model (PBX-mouse) as previously described in Inoue et. al (Hepatology. 2007 April; 45(4):921-8) and Tenato et. al. (Am J Pathol 2004; 165-901-912) with the following specification: Test animals: HCV Gla-infected PXB-mice, male or female, >70% replacement index of human hepatocytes. Dosing was performed p.o for 7 days at doses indicated below wherein QD represents a single dose per day, BID represents two doses per day.

Efficacy of compound 8a was compared to CAS-1375074-52-4. Results are indicated in FIG. 1. The FIGURE shows the log drop HCV viral RNA after dosing for a period of 7 days.

FIG. 1 clearly shows that a dosing of 100 mg/kg QD for CAS 1375074-52-4 (indicated as *, n=4) does not result in a significant log drop in HCV viral RNA. This in strong contrast to each of the indicated dose regimens for compound 8a, were a clear log drop is observed for 100 mg/kg QD (indicated as ♦, n=3), 200 mg/kg QD (indicated as ●, n=4), 50 mg/kg BID (indicated as ■, n=4). The most pronounced log drop effect in viral RNA is observed after a 7 day dosing of compound 8a at 100 mg/kg BID (indicated as ▲, n=4).

The invention claimed is:

1. A method of preparing compound of formula (3),

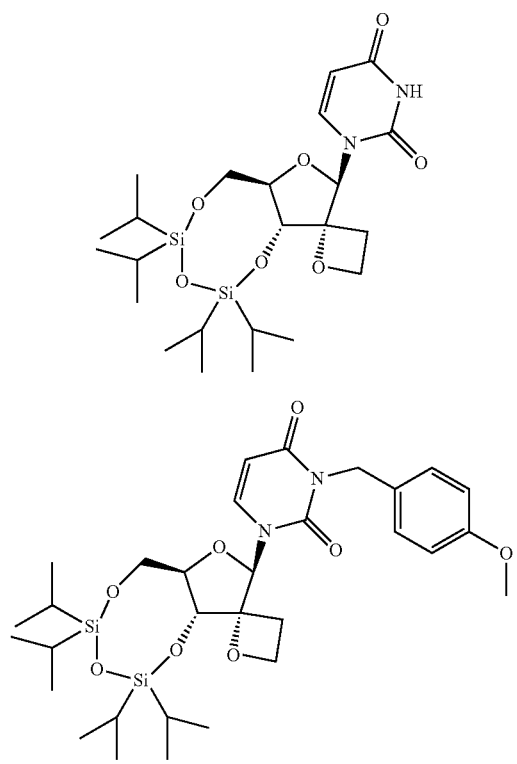

comprising reacting compound of formula (2) with 4-methoxybenzyl chloride.

2. A method as claimed in claim 1, wherein said reacting compound of formula (2) with 4-methoxybenzyl chloride takes place in the presence of 1,8-diazabicyclo[5.4.0]undec-7-ene (DBU).

3. A method as claimed in claim 1, further comprising reacting compound of formula (1)

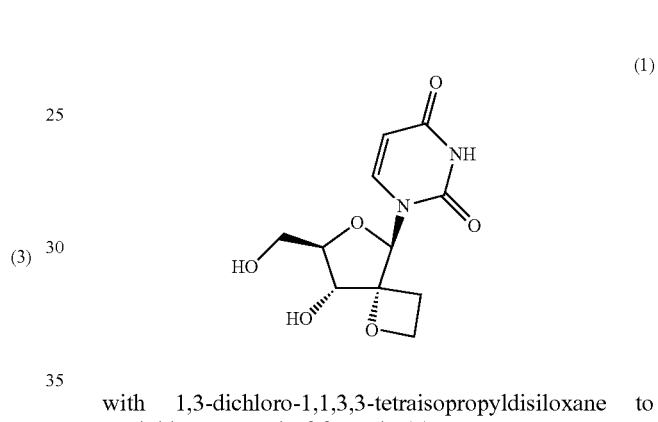

with 1,3-dichloro-1,1,3,3-tetraisopropyldisiloxane to yield compound of formula (2).

4. A method as claimed in claim 3, wherein said reacting compound of formula (1) with 1,3-dichloro-1,1,3,3-tetraisopropyldisiloxane takes place in the presence of pyridine.

* * * * *

SEQUENCE LISTING

<160> NUMBER OF SEQ ID NOS: 8

<210> SEQ ID NO 1
<211> LENGTH: 41
<212> TYPE: DNA
<213> ORGANISM: Hepatitis C virus
<220> FEATURE:
<221> NAME/KEY: source
<222> LOCATION: 1..41
<223> OTHER INFORMATION: /mol_type="unassigned DNA"
    /organism="Hepatitis C virus"

<400> SEQUENCE: 1
ggccgtcatg gtggcgaata agtctagcca tggcgttagt a                    41

<210> SEQ ID NO 2
<211> LENGTH: 20
<212> TYPE: DNA
<213> ORGANISM: Hepatitis C virus
<220> FEATURE:
<221> NAME/KEY: source
<222> LOCATION: 1..20
<223> OTHER INFORMATION: /mol_type="unassigned DNA"
    /organism="Hepatitis C virus"

<400> SEQUENCE: 2
ctcccggggc actcgcaagc                                            20

<210> SEQ ID NO 3

```
<211> LENGTH: 20
<212> TYPE: DNA
<213> ORGANISM: Hepatitis C virus
<220> FEATURE:
<221> NAME/KEY: source
<222> LOCATION: 1..20
<223> OTHER INFORMATION: /mol_type="unassigned DNA"
      /organism="Hepatitis C virus"

<400> SEQUENCE: 3
gtctagccat ggcgttagta                                              20

<210> SEQ ID NO 4
<211> LENGTH: 21
<212> TYPE: DNA
<213> ORGANISM: Hepatitis C virus
<220> FEATURE:
<221> NAME/KEY: source
<222> LOCATION: 1..21
<223> OTHER INFORMATION: /mol_type="unassigned DNA"
      /organism="Hepatitis C virus"

<400> SEQUENCE: 4
ggccgtcatg gtggcgaata a                                            21

<210> SEQ ID NO 5
<211> LENGTH: 20
<212> TYPE: DNA
<213> ORGANISM: Hepatitis C virus
<220> FEATURE:
<221> NAME/KEY: source
<222> LOCATION: 1..20
<223> OTHER INFORMATION: /mol_type="unassigned DNA"
      /organism="Hepatitis C virus"

<400> SEQUENCE: 5
ctttcgcgac ccaacactac                                              20

<210> SEQ ID NO 6
<211> LENGTH: 20
<212> TYPE: DNA
<213> ORGANISM: Hepatitis C virus
<220> FEATURE:
<221> NAME/KEY: source
<222> LOCATION: 1..20
<223> OTHER INFORMATION: /mol_type="unassigned DNA"
      /organism="Hepatitis C virus"

<400> SEQUENCE: 6
agagccatag tggtctgcgg                                              20

<210> SEQ ID NO 7
<211> LENGTH: 19
<212> TYPE: DNA
<213> ORGANISM: Hepatitis C virus
<220> FEATURE:
<221> NAME/KEY: source
<222> LOCATION: 1..19
<223> OTHER INFORMATION: /mol_type="unassigned DNA"
      /organism="Hepatitis C virus"

<400> SEQUENCE: 7
ttgaaaatcc gggggagag                                               19

<210> SEQ ID NO 8
<211> LENGTH: 20
<212> TYPE: DNA
<213> ORGANISM: Hepatitis C virus
<220> FEATURE:
```

```
<221> NAME/KEY: source
<222> LOCATION: 1..20
<223> OTHER INFORMATION: /mol_type="unassigned DNA"
      /organism="Hepatitis C virus"

<400> SEQUENCE: 8
acattgttcc aacatgccag                                              20
```